United States Patent
McDermott

(10) Patent No.: US 11,000,673 B2
(45) Date of Patent: *May 11, 2021

(54) CATHETER POSITIONING

(71) Applicant: Covidien LP, Mansfield, MA (US)

(72) Inventor: Sean McDermott, Hanson, MA (US)

(73) Assignee: Covidien LP, Mansfield, MA (US)

( * ) Notice: Subject to any disclaimer, the term of this patent is extended or adjusted under 35 U.S.C. 154(b) by 193 days.

This patent is subject to a terminal disclaimer.

(21) Appl. No.: 16/186,794

(22) Filed: Nov. 12, 2018

(65) Prior Publication Data
US 2019/0076624 A1 Mar. 14, 2019

Related U.S. Application Data

(63) Continuation of application No. 14/227,143, filed on Mar. 27, 2014, now Pat. No. 10,155,100.

(51) Int. Cl.
*A61M 25/01* (2006.01)
*A61M 25/00* (2006.01)
(Continued)

(52) U.S. Cl.
CPC ...... *A61M 25/0108* (2013.01); *A61M 25/007* (2013.01); *A61M 25/0043* (2013.01);
(Continued)

(58) Field of Classification Search
CPC ............ A61M 25/0043; A61M 1/3661; A61M 2025/0057; A61M 25/0108
See application file for complete search history.

(56) References Cited

U.S. PATENT DOCUMENTS 4,840,622 A * 6/1989 Hardy ............... A61M 25/0052
604/264
5,195,962 A 3/1993 Martin et al.
(Continued)

FOREIGN PATENT DOCUMENTS

CN 1878583 A 12/2006
CN 101132749 A 2/2008
(Continued)

OTHER PUBLICATIONS

Fourth Office Action, and machine translation thereof (from the Global Dossier), from counterpart Chinese Application No. 201510137661.3 dated Nov. 26, 2019, 16 pp.
(Continued)

*Primary Examiner* — Bradley J Osinski
(74) *Attorney, Agent, or Firm* — Shumaker & Sieffert, P.A.

(57) ABSTRACT

A medical catheter includes an elongate member and an insert. The elongate member has proximal and distal end portions and defines a longitudinal axis through the proximal and distal end portions. The elongate member includes a wall at least partially defining a longitudinal lumen and defining a side opening extending radially from an outer surface of the wall to the longitudinal lumen. The insert is at least partially disposed within the side opening and at least partially defines an insert passage in fluid communication with the longitudinal lumen. The elongate member includes a first material defining the side opening and the insert includes a second material different from the first material.

13 Claims, 7 Drawing Sheets

(51) Int. Cl.
*A61M 1/36* (2006.01)
*A61B 90/00* (2016.01)

(52) U.S. Cl.
CPC .... *A61B 2090/3966* (2016.02); *A61M 1/3661* (2014.02); *A61M 25/0068* (2013.01); *A61M 2025/0031* (2013.01); *A61M 2025/0057* (2013.01); *A61M 2025/0073* (2013.01)

(56) References Cited

U.S. PATENT DOCUMENTS

| | | |
|---|---|---|
| 5,827,231 A | 10/1998 | Harada |
| 7,141,035 B2 | 11/2006 | Haggstrom |
| 8,821,562 B2 | 9/2014 | Bourang et al. |
| 10,155,100 B2 | 12/2018 | McDermott |
| 2004/0122465 A1* | 6/2004 | McMurtry .......... A61M 25/104 606/194 |
| 2004/0215162 A1 | 10/2004 | Putz |
| 2006/0142703 A1* | 6/2006 | Carter ............... A61M 25/0052 604/264 |
| 2006/0167398 A1 | 7/2006 | Solar et al. |
| 2006/0257355 A1 | 11/2006 | Stewart et al. |
| 2007/0191810 A1* | 8/2007 | Kennedy .......... A61M 25/0015 604/508 |
| 2008/0172011 A1 | 7/2008 | Heroux et al. |
| 2009/0306605 A1 | 12/2009 | Amano et al. |
| 2012/0077049 A1 | 3/2012 | Lin |
| 2013/0110083 A1 | 5/2013 | Koehler |

FOREIGN PATENT DOCUMENTS

| | | |
|---|---|---|
| CN | 103533967 A | 1/2014 |
| CN | 203408343 U | 1/2014 |
| EP | 2316518 A1 | 5/2011 |
| WO | 2006002192 A2 | 1/2006 |
| WO | 2006062873 A1 | 6/2006 |
| WO | 2007095252 A1 | 8/2007 |

OTHER PUBLICATIONS

Third Office Action, and machine translation thereof (from the Global Dossier), from counterpart Chinese Application No. 201510137661.3 dated Sep. 30, 2019, 15 pp.

Extended Search Report from counterpart European Application No. 15158416.6, dated Jul. 14, 2015, 9 pp.

Notification of the First Office Action, and translation thereof, from counterpart Chinese Application No. 201510137661.3, dated Aug. 18, 2017, 12 pp.

Rejection Decision, and translation thereof, from counterpart Chinese Application No. 201510137661.3, dated Jun. 12, 2018, 7 pp.

Prosecution History from U.S. Appl. No. 14/227,143, dated Sep. 28, 2015 through Oct. 19, 2018, 157 pp.

Notification of Reexamination, and translation thereof, from counterpart Chinese Application No. 201510137661.3, dated Apr. 9, 2019, 11 pp.

Examination Report from counterpart European Application No. 15158416.6 dated Dec. 7, 2018, 3 pp.

Response to Examination Report from counterpart European Application No. 15158416.6, dated Dec. 7, 2018, 16 pp., filed on Feb. 12, 2019.

Notification of Rejection, and partial English translation thereof, from counterpart Chinese Application No. 201510137661.3, dated Jun. 17, 2020, 7 pp.

* cited by examiner

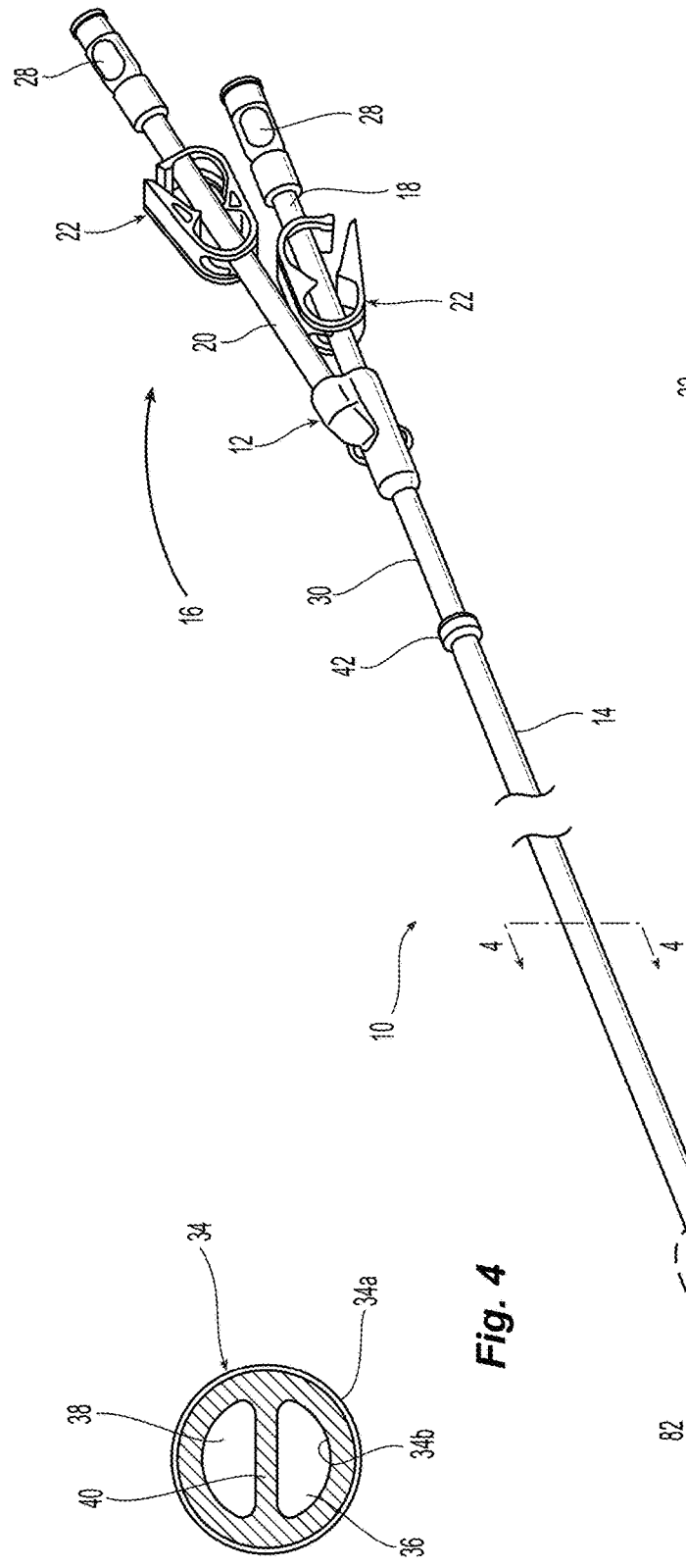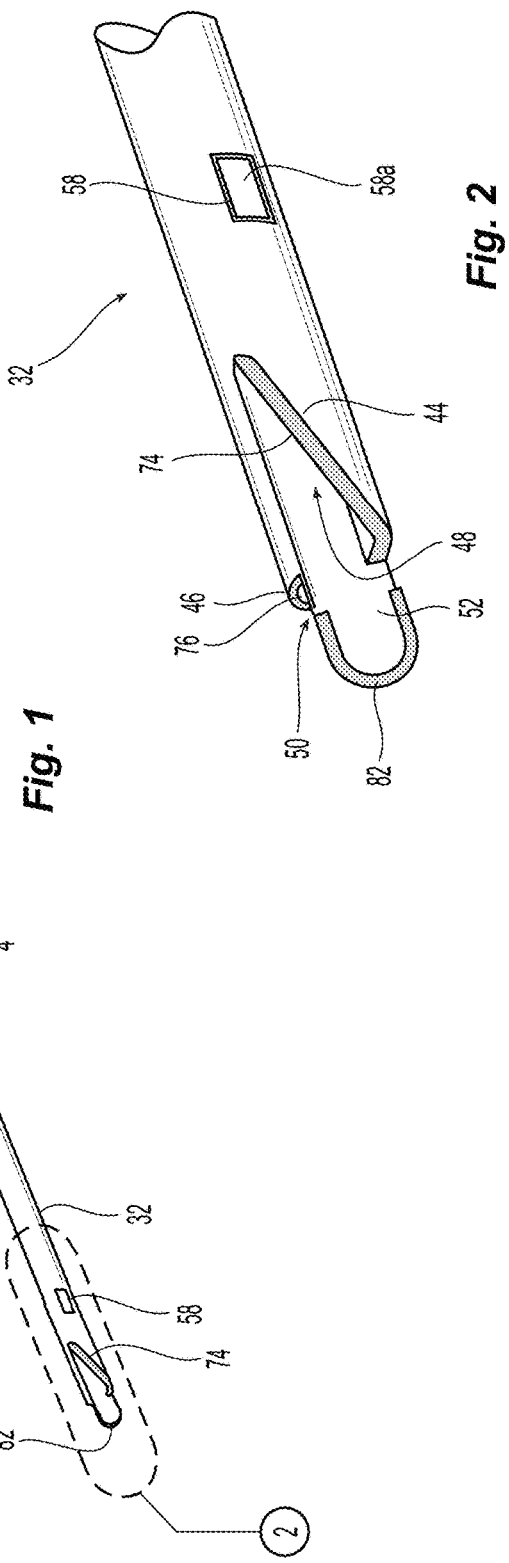

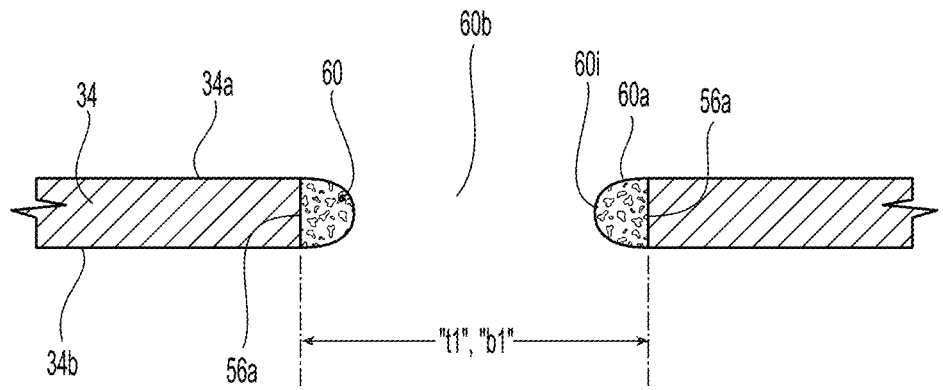
*Fig. 9*
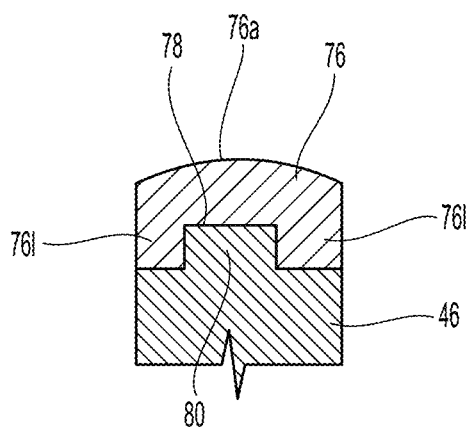 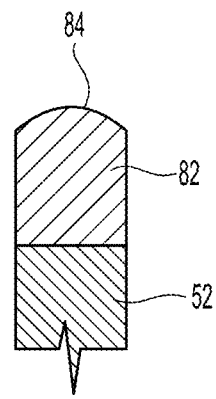
*Fig. 10*  *Fig. 11*

CATHETER POSITIONING

CROSS-REFERENCE TO RELATED APPLICATION

This application is a continuation of U.S. patent application Ser. No. 14/227,143 filed Mar. 27, 2014, and entitled, "CATHETER POSITIONING," the entire content of which is incorporated herein by reference.

BACKGROUND

Catheters are flexible medical instruments for use in the introduction and withdrawal of fluids to and from body cavities, ducts, and vessels. Catheters are utilized in many different applications within the human body, including the administration of liquid therapeutic agents and the removal of bodily fluids for testing, monitoring, or disposal.

For example, catheters are used in hemodialysis procedures, in which blood is withdrawn from a blood vessel, directed to a hemodialysis unit for dialysis or purification, and subsequently returned to the blood vessel. Hemodialysis catheters can define an arterial lumen and a venous lumen. Blood is withdrawn from the patient through the arterial lumen and delivered to a dialyzer. Treated blood is returned to the patient, from the dialyzer, through the venous lumen. Positional occlusion can occur as a result of distal openings at the catheter tip being pressed against a vessel wall.

SUMMARY

The present disclosure is directed to catheters including at least one insert (e.g., at least one of a side insert, a septum extension insert, or an end wall insert) disposed along at least a portion of one or more openings defined by a catheter body. As compared to catheters without such inserts, the presently disclosed catheters are more easily positioned positioning in a body lumen to reduce, for example, the likelihood of positional occlusion and/or to improve treatment effectiveness.

In one aspect, a medical catheter includes an elongate member and an insert. The elongate member has proximal and distal end portions and defines a longitudinal axis through the proximal and distal end portions. The elongate member includes a wall at least partially defining a longitudinal lumen and defining a side opening extending radially from an outer surface of the wall to the longitudinal lumen. The insert is at least partially disposed within the side opening and at least partially defines an insert passage in fluid communication with the longitudinal lumen. The elongate member includes a first material defining the side opening and the insert includes a second material different from the first material.

In some embodiments, the side opening is disposed more toward a distal end portion than toward a proximal end portion of the elongate member. In certain embodiments, a portion of the insert disposed within the side opening is dimensioned to approximate an inner boundary defined by the side opening. In some embodiments, the insert has an outer periphery greater than an inner boundary of the side opening. In certain embodiments, at least a portion of the insert is secured to a portion of the wall defining the side opening. The insert can have at least one radiused surface along the insert passage.

In some embodiments, the second material of the side insert includes at least one of an anti-thrombogenic agent and an antimicrobial agent. In certain embodiments, the second material of the side insert is more radiopaque than the first material of the elongate member. In some embodiments, the second material has a higher durometer than the first material. The second material may include at least one of a metal (e.g., titanium and stainless steel) and a polymer (e.g., polytetrafluoroethylene and polyurethane having a Shore A hardness greater than 95 durometer). For example, the insert can include a radiopaque core at least partially disposed within a polymer.

In another aspect, a medical catheter includes an elongate member a first insert and a second insert. The elongate member has proximal and distal end portions and defines a longitudinal axis extending through the proximal and distal end portions. The elongate member includes a wall at least partially defining a first lumen and a second lumen, and defining first and second side openings in fluid communication with the respective first and second lumens. The first insert is at least partially disposed within the first side opening, and the second insert is at least partially disposed within the second side opening. The elongate member includes a first material defining the first and second side openings, and the first and second inserts each include a second material different from the first material.

In some embodiments, the second material is more radiopaque than the first material. In certain embodiments, the second material includes at least one of titanium, stainless steel, polytetrafluoroethylene, and polyurethane having a Shore A hardness greater than 95 durometer. Additionally or alternatively, at least one of the first and second inserts may include at least one of an anti-thrombogenic agent and an antimicrobial agent.

In another aspect, a medical catheter includes an elongate member and an extension insert. The elongate member has proximal and distal end portions and defines a longitudinal axis extending through the proximal and distal end portions. The elongate member includes a wall, a septum, and a septum extension. The septum is disposed within the wall such that the wall and the septum together define a first lumen and a second lumen. The septum extends to the septum extension disposed distal to the first and second lumens. The extension insert is at least partially disposed on the septum extension. The septum extension includes a first material and the extension insert includes a second material different from the first material.

In some embodiments, the second material may be more radiopaque than the first material. Additionally or alternatively, the extension insert can include at least one of an anti-thrombogenic agent and an antimicrobial agent.

In certain embodiments, the medical catheter further includes a wall insert. The distal end portion of the elongate member defines first and second axial openings in fluid communication with the respective first and second lumens, and the wall insert is disposed along at least one of the first and second axial openings. The wall insert may include a material different from a material of the distal end portion of the elongate tubular member.

Embodiments can include one or more of the following advantages.

In some embodiments, the side insert, the wall insert and/or the septum extension insert can reduce the likelihood of thrombus formation in areas in which blood enters and exits an elongate member. For example, as compared to catheters without inserts, the side insert, the wall insert, and/or the septum extension insert can enclose rough or sharp edges, possibly developed during manufacture of the catheter. Additionally or alternatively, the side inserts, the wall insert, and/or the septum extension insert can have radiused blood contacting surfaces to reduce shear stresses on blood entering and exiting the elongate member.

In certain embodiments, the side insert, the wall insert, and/or the septum extension insert can include a material that differs in radiopacity (e.g., is more radiopaque) from a material forming the elongate member in the vicinity of the insert(s). As compared to catheters without such a difference in radiopacity, catheters including the side insert, the wall insert, and/or the septum extension insert can facilitate positioning and/or orienting the elongate member in the vasculature of a subject using radiological techniques (e.g., fluoroscopy).

In some embodiments, the side insert, the wall insert, and/or the septum extension insert can include therapeutic agents impregnated or coated on the inserts. As compared to catheters without such inserts, inserts including therapeutic agents can improve treatment by, for example, providing an anti-thrombotic and/or antimicrobial effect on blood moving past the inserts.

Other aspects, features, and advantages will be apparent from the description, drawings, and the claims.

BRIEF DESCRIPTION OF THE DRAWINGS

FIG. 1 is a perspective view of a catheter including a catheter hub and an elongate member extending from the catheter hub.

FIG. 2 is an enlarged perspective view of a distal end portion of the elongate member of FIG. 1, taken along the area of detail identified in FIG. 1.

FIG. 4 is a cross-sectional view of the elongate member of the catheter of FIG. 1, taken along the lines 4-4 of FIG. 1.

FIG. 9 is a cross-sectional view of a side opening of the elongate member of FIG. 1, taken along the lines 9-9 of FIG. 6, with a side insert shown positioned within a side opening.

FIG. 10 is a cross-sectional view taken along the lines 10-10 of FIG. 6, with a wall insert shown adjacent an end wall of the elongate member of FIG. 1.

FIG. 11 is a cross-sectional view taken along the lines 11-11 of FIG. 6, with a septum extension insert shown mounted to a septum extension of the elongate member of FIG. 1.

DETAILED DESCRIPTION

Figure 3:
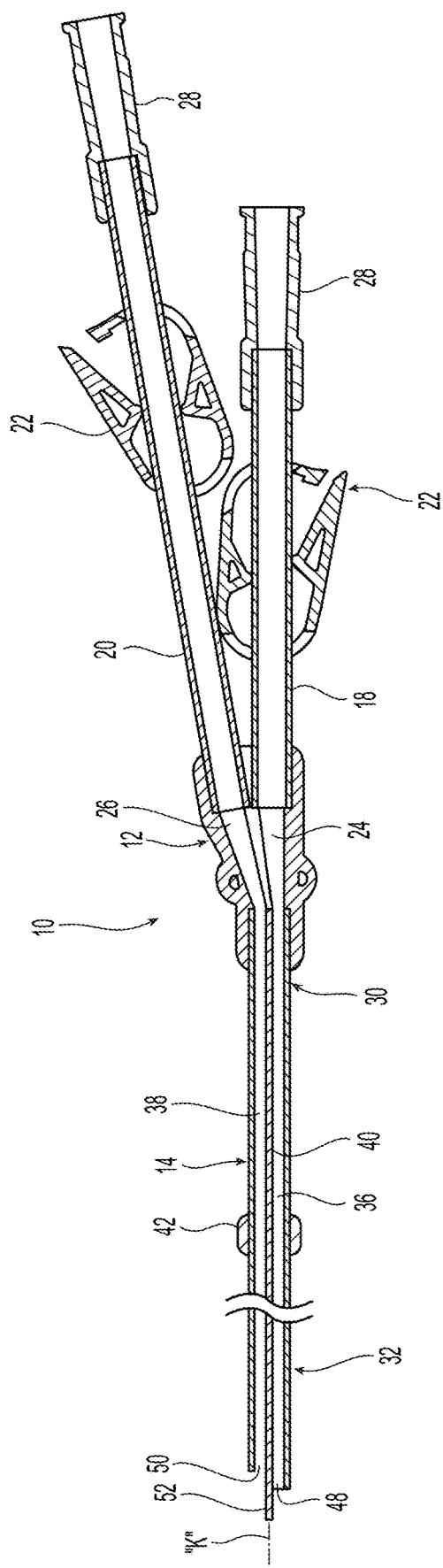
FIG. 3 is a side cross-sectional view of the catheter of FIG. 1.
Figure 5:
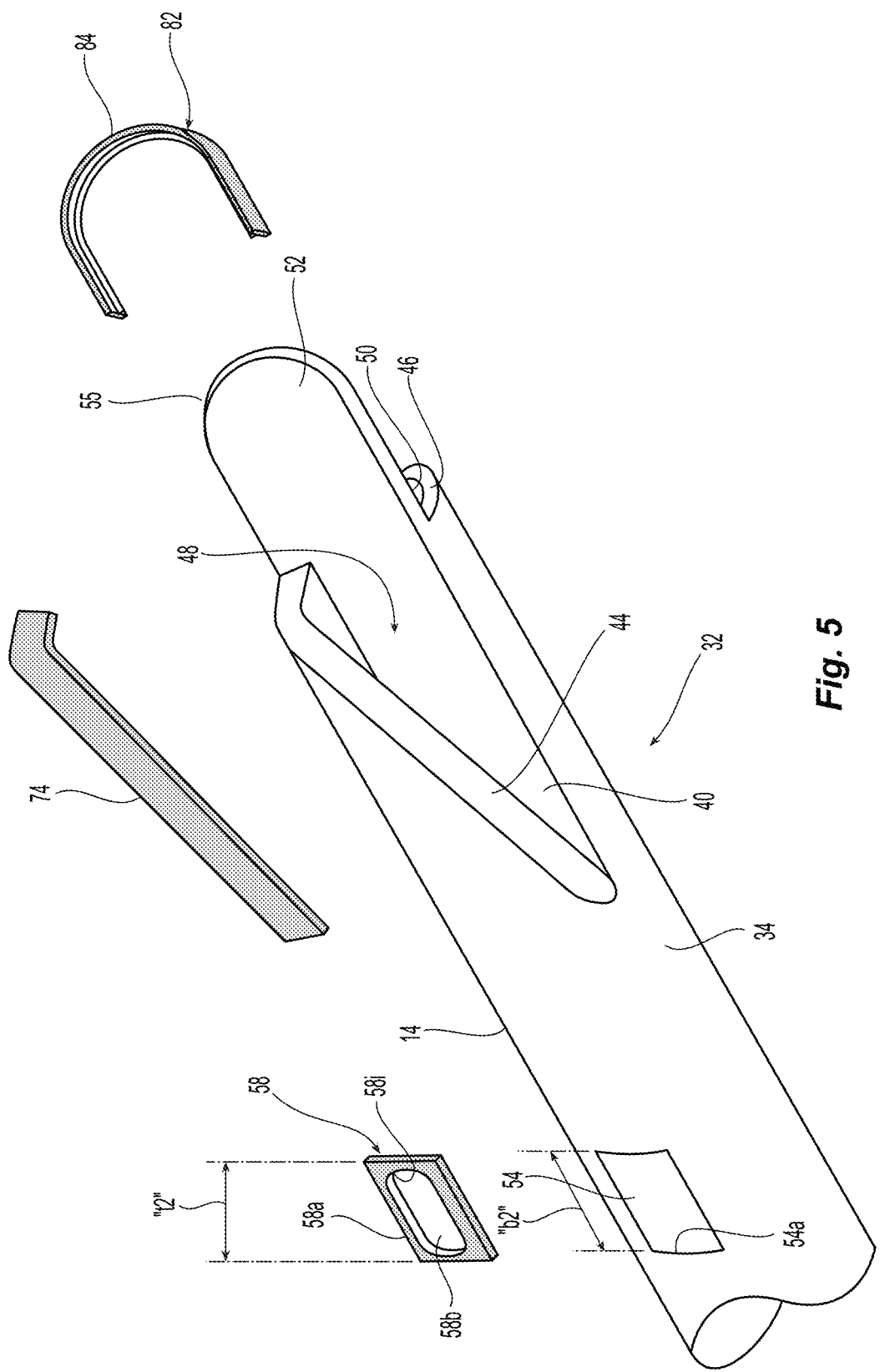
FIG. 5 is a partially exploded perspective view of the distal end portion of the elongate member shown in FIG. 2.
Figure 6:
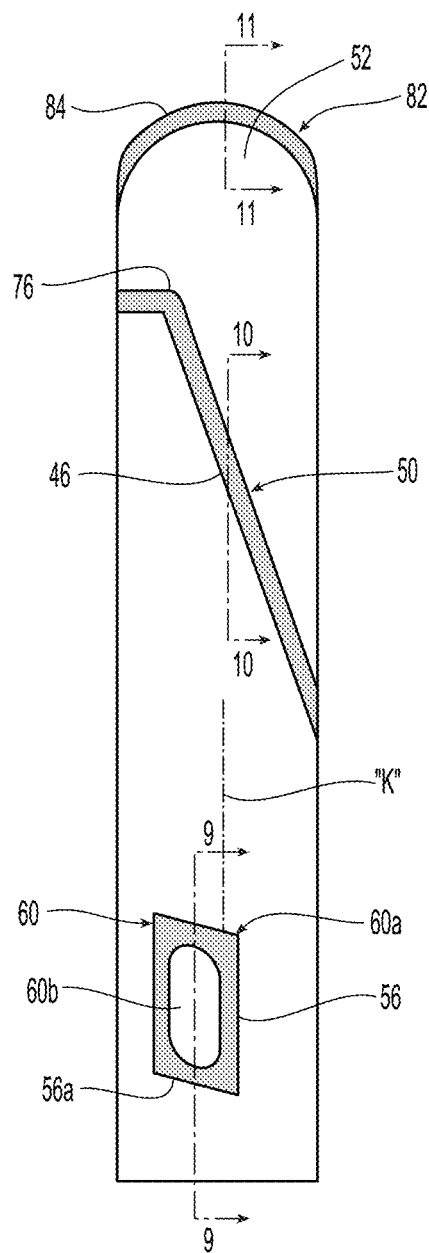
FIG. 6 is a side view of the distal end portion of the elongate member shown in FIG. 2.
Figure 8:
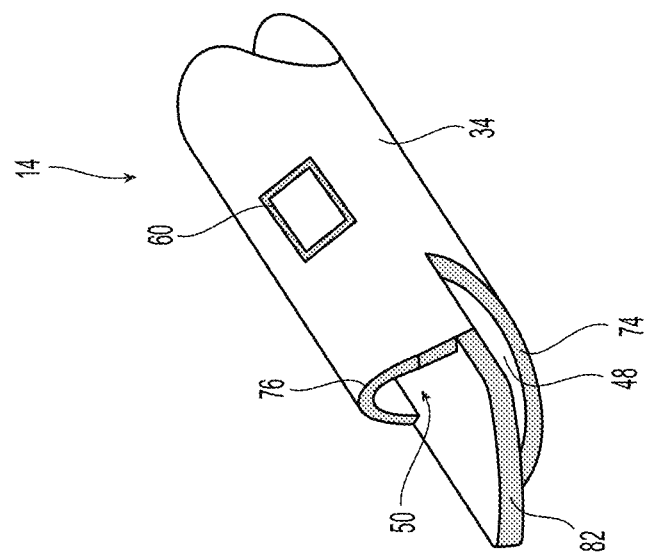
FIGS. 7-8 are perspective views of the distal end portion of the elongate member shown in FIG. 2.
Figure 7:
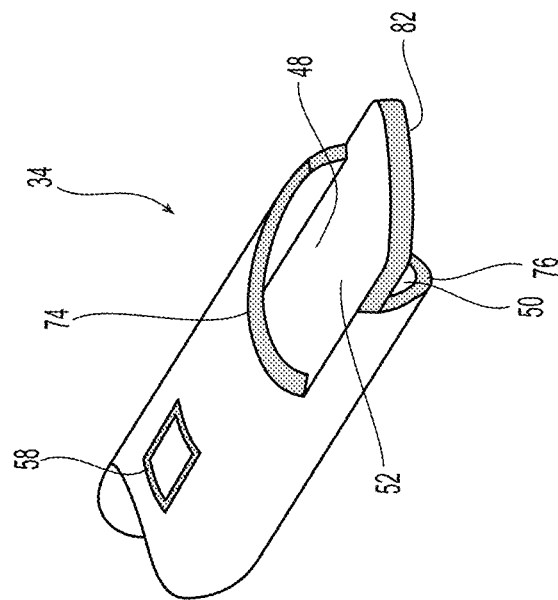

As used herein, the term "proximal" refers to the portion of a structure closer to a clinician, and the term "distal" refers to the portion of the structure further from the clinician. As used herein, the term "subject" refers to a human subject or other animal. The term "clinician" refers to a doctor, nurse or other care provider and may include support personnel.

Referring now to FIGS. 1-9, a catheter 10 includes a hub 12, an elongate member 14, and an extension tube assembly 16. The hub 12 is secured (e.g., releasably secured) to a proximal end portion 30 of the elongate member 14 and to the extension tube assembly 16 such that the elongate member 14 and the extension tube assembly 16 are in fluid communication with one another. As described in further detail below, first and second side inserts 58, 60 are disposed along a distal end portion 32 of the elongate member 14, with each side insert 58, 60 defining respective side flow passages 58b, 60b for passage of fluids e.g., for the passage of blood in a hemodialysis procedure). The first and second side inserts 58, 60 are made of a material that differs from the material of the elongate member 14 in the vicinity of the first and second side inserts 58, 60. As described in further detail below, such a difference in material can improve the performance of the catheter 10 as compared to a catheter without such a difference in material.

For example, as described in further detail below, the material of first and second side inserts 58, 60 can be more radiopaque than the material of the elongate member 14 in the vicinity of the first and second side inserts 58, 60 to facilitate positioning and/or orienting the elongate member 14 in the vasculature of a subject using radiological techniques (e.g., fluoroscopy). As compared to catheters including circumferential marker bands proximal or distal to side holes, the side inserts 58, 60, by at least partially defining the side flow passages 58b, 60b themselves, can facilitate more accurate placement of the side flow passages 58b, 60b. Additionally or alternatively, as compared to catheters including circumferential marker bands, the side inserts 58, 60 can facilitate radial identification the side flow passages 58b, 60b. As an example, the appearance of the side inserts 58, 60 as a single shape is an indication that the side inserts 58, 60 are each substantially perpendicular to the direction of fluoroscopy.

The proximal end portion 30 and the distal end portion 32 of the elongate member 14 define a longitudinal axis "k." In some embodiments, the elongate member 14 is sufficiently flexible for use as a chronic hemodialysis catheter. For example, the elongate member 14 may be formed of silicone or biocompatible polyurethane.

The elongate member 14 is a dual lumen catheter including an outer wall 34 and a septum wall 40, each extending along the length of the elongate member 14. Together, the outer wall 34 and the septum wall 40 define at least a portion of first and second longitudinal lumens 36, 38. The first and second longitudinal lumens 36, 38 may define, for example, a kidney-shaped, circular, pie-shaped, and/or D-shaped cross-section perpendicular to the longitudinal axis "k." Additionally or alternatively, the first and second longitudinal lumens 36, 38 can be coaxial.

The outer wall 34 terminates at first and second end walls 44, 46, which are separated by the septum 40. The pair of opposed axial openings 48, 50 are at least partially defined by the respective end walls 44, 46 and the septum 40. The axial openings 48, 50 are in fluid communication with respective first and second longitudinal lumens 36, 38. In embodiments, the first and second end walls 44, 46 and corresponding axial openings 48, 50 may be symmetrically disposed about the septum 40. The symmetry of the distal end portion 32 may facilitate reversible or alternating flow between the first and second longitudinal lumens 36, 38. For example, the catheter 10 may be used in forward or reverse flow modes such that either one of the first and second longitudinal lumens 36, 38 may operate as the arterial or venous lumen during hemodialysis. The reversibility of the distal end portion 32 may, for example, facilitate clearance of thrombus and/or facilitate redirection of flow in the event of positional occlusion.

The distal end portion 32 of the elongate member 14 may further include a septum extension 52 extending from the septum 40, beyond the first and second end walls 44, 46 and axial openings 48, 50. The septum extension 52 can include an arcuate end surface 55 to facilitate, for example, passage of the distal end portion 32 of the elongate member 14 through the vasculature.

The elongate member 14 further defines first and second side openings 54, 56 extending through the outer wall 34 of the elongate member 14, from an outer wall surface 34a to an inner wall surface 34b. The first and second side openings 54, 56 are in fluid communication with the respective first and second longitudinal lumens 36, 38 and axial openings 48, 50. In some embodiments, the open area defined by each of the first and second side openings 54, 56 approximately equals the open area of the respective first and second axial openings 48, 50.

The first and second side openings 54, 56 are spaced proximally from the axial openings 48, 50 of the elongate member 14 along the longitudinal axis "k." The first and second side openings 54, 56 are along the distal end portion 32 of the elongate member 14. In some embodiments, the first and second side openings 54, 56 are symmetric with respect to the septum 40 (e.g., the first and second side openings can be diametrically opposed to one another).

The side openings 54, 56 support the respective first and second side inserts 58, 60 such that the first and second side inserts 58, 60 define the respective side flow passages 58b, 60b. In use, blood or other fluid moving through the elongate member 14 can flow through the side flow passages 58b, 60b and/or through the respective axial openings 48, 50. The combination of side flow passages 58b, 60b and axial openings 48, 50 can, for example, result in low (e.g., less than 5%) recirculation of treated blood during a hemodialysis procedure. Additionally or alternatively, as compared to an elongate member without side flow passages, the combination of side flow passages 58b, 60b and axial openings 48, 50 can reduce the likelihood of positional occlusion of the catheter 10.

As shown in FIGS. 5-9, each of the first and second side inserts 58, 60 is at least partially positioned within the respective side openings 54, 56. In some embodiments, the first and second side inserts 58, 60 are substantially identical to one another with respect to at least one of size, shape, surface finish, and composition. Such symmetry can, for example, facilitate the use of the catheter 10 in any of various configurations with minimal impact on performance of the catheter.

The side inserts 58, 60 each include a respective base 58a, 60a at least partially defining the respective side flow passage 58b, 60b through the respective side insert 58, 60. The bases 58a, 60a are each positioned within the respective side openings 54, 56 and secured to the wall surfaces 54a, 56a defining the side opening 54, 56. For example, the bases 58a, 60a can be secured to the respective surfaces 54a, 56a through one or more of RF welding, over-molding, heat-swaging, and adhesives. Each side insert 58, 60 can cover rough edges which may be present as a result of a cutting or punching process used to form the side openings 54, 56 within the elongate member 14 during manufacture. Thus, it should be appreciated that, the side inserts 58, 60 can be provide a smoother surface over which blood may flow during use, as compared to catheters with side slots that do not have side inserts. By reducing shear stress on blood moving into and out of the catheter 10, the smoother surface of the side inserts 58, 60 can, for example, reduce the likelihood of thrombus formation during use.

Each of the first and second inserts 58, 60 is shown as generally corresponding to the shape of the respective side openings 54, 56 along which it is positioned. The outer boundary "t1" of the base 60a of the side insert 60 generally approximates the internal boundary "b1" of the side opening 56 in which it is positioned. Similarly, the outer boundary "t2" of the base 58a of the side insert 58 generally approximates the internal boundary "b2" of the side opening 54 in which it is positioned.

The inner surfaces 58i, 60i of each of the first and second side inserts 58, 60 surrounding and defining the side flow passages 58b, 60b are generally smooth. The inner surfaces 58i, 60i can be atraumatic. For example, as compared to edges of side holes of catheters without side inserts, the inner surfaces 58i, 60i can have substantially rounded edges with a radius of curvature substantially equal to (within about 10%) of the wall thickness of the elongate member 14. As compared to methods of reducing the likelihood of thrombus formation near side flow passages without side inserts, such atraumatic inner surfaces 58i, 60i can reduce complexity associated with reducing the likelihood of thrombus formation.

The material of the side inserts 58, 60 can have a higher durometer than the material of the elongate member 14 and/or the wall surfaces 54a, 56a adjacent the side openings 54, 56. As compared to lower durometer material, the higher durometer of the material of the side inserts 58, 60 can, for example, facilitate shaping the side inserts 58, 60 to have atraumatic surfaces of the type described above. Additionally or alternatively, the higher durometer material of the side inserts 58, 60 can facilitate mechanically securing the side inserts 58, 60 to the elongate member 14.

In some embodiments, the first and second side inserts 58, 60 are more radiopaque than the material of the elongate member 14 in the vicinity of the first and second side inserts 58, 60. As compared to catheters without side inserts, the difference in radiopacity provided by the side inserts 58, 60 can facilitate, verification of the position and/or orientation of the side flow passages 58b, 60b at a desired intravascular site using a radiological technique (e.g., fluoroscopy). For example, in hemodialysis applications, a radiopaque contrast between the material of the first and second inserts 58, 60 and the material of the elongate member 14 can facilitate the use of fluoroscopy to verify position and/or orientation of the distal end portion 32 of the elongate member 14 in accordance with a standard such as the standard described in National Kidney Foundation, Kidney Disease Outcomes Quality Initiative (KDOQI), Updates Clinical Practice Guidelines and Recommendations, Hemodialysis Adequacy, Peritoneal Dialysis Adequacy, Vascular Access, (2006).

The side inserts 58, 60 can be formed of radiopaque metals such as stainless steel and/or titanium. For example, the side inserts 58, 60 can be formed through a stamping operation. The metals used to form the side inserts 58, 60 may be acid washed during manufacture to remove any burrs formed during manufacture to smooth the outer finish of the side inserts 58, 60.

Additionally or alternatively, radiopaque materials that form the side inserts 58, 60 can include a polymeric material with a metal (e.g., barium) core and/or impregnated with metal flakes. The polymeric material can include, for example, a biocompatible polymer such as one or more of polytetrafluoroethylene (PTFE) and a high durometer polyurethane having a Shore A hardness greater than 95 durometer. A molding process can be used to form the side inserts 58, 60 from a biocompatible polymer such that the side inserts 58, 60 are generally smooth.

In some embodiments, at least one cuff 42 is mounted about the outer wall 34 of the elongate member 14. The cuff 42 may permit tissue ingrowth for long term securing of elongate member 14 in an indwelling position. The cuff 42 can include, for example, a fabric material adhered to the elongate member 14.

The catheter hub 12 may be any hub-type suitable for the intended application of the catheter 10, and may be fabricated from polymeric materials and/or stainless steel. In a hemodialysis application, for example, the catheter hub 12 may define first and second internal hub channels 24, 26 in fluid communication with the first and second longitudinal lumens 36, 38 of the elongate member 14. While the catheter hub 12 is shown as having asymmetrical y-shape, it should be appreciated that the catheter hub 12 can have a symmetrical y-shape without departing from the scope of the present disclosure.

The catheter 10 may include an extension tube assembly 16 including first and second extension tubes 18, 20 with attached luer adapters 28. Clamps 22 may be mounted to the extension tubes 18, 20 to control fluid flow.

In use, the catheter 10 is inserted into the vasculature of a subject. Verification of the position and/or radial orientation of the distal end portion 32 of the elongate member 14 is confirmed via fluoroscopy of the radiopaque material associated with the side inserts 58, 60.

In a hemodialysis application, the catheter 10 is connected to a hemodialysis machine and blood is withdrawn and returned through the first and second longitudinal lumens 36, 38 of the elongate member 14. Blood flowing into and out of the catheter 10 may pass through the side flow passages 58b, 60b defined by the atraumatic surfaces of the side inserts 58, 60.

While certain embodiments have been described, other embodiments are additionally or alternatively possible.

For example, while catheters have been described as including side inserts defining side flow passages for passage of fluids into and out of elongate members, other types of inserts can additionally or alternatively be disposed along portions of the elongate members. For example, with reference to FIGS. 5-8 and 10, the elongate member 14 may additionally or alternatively include one or more wall inserts 74, 76 mounted to the end walls 44, 46 of the elongate member 14 adjacent the axial openings 48, 50. The wall inserts 74, 76 may include, for example, a radiopaque material to facilitate positioning of the axial openings 48, 50 within the vasculature of a subject. It should be appreciated that the wall inserts 74, 76 can include any of the materials described herein with respect to the side inserts 58, 60.

The wall inserts 74, 76 may be generally U-shaped, each defining a channel 78 positionable over an end face of the respective end wall 44, 46. The U-shape of the wall inserts 74, 76 can facilitate, for example, securement of the wall inserts 74, 76 to the elongate member 14. Additionally or alternatively, the U-shape of the wall inserts 74, 76 can facilitate alignment of the wall inserts 74, 76 with the axial openings 48, 50.

As shown in FIG. 10, in some embodiments, the end wall 46 defines a stepped cross-section with a reduced segment 80 received within a channel 78 defined by the wall insert 76. In these embodiments, the stepped configuration of the end wall 46 accommodates legs 761 of the wall insert 76 such that the outer dimension of the wall, inclusive of the wall insert 76, is substantially continuous (e.g., varying by less than about 2%) to reduce the likelihood of thrombus formation in the vicinity of the wall inserts 74, 76. The wall insert 76 may have a curved or radiused outer surface 76a to reduce the likelihood of potential blood shearing and consequent clotting. In certain embodiments, the end walls 44, 46 are directly bonded (e.g., adhesively bonded) to the end walls 44, 46. It should be appreciated that the wall insert 74 would have an identical configuration to the wall insert 76.

As another example, referring to FIGS. 5-8 and 11, the elongate member 14 may additionally or alternatively include a septum extension insert 82 secured to the septum extension 52. The septum extension insert 52 may include, for example, a radiopaque material to facilitate positioning of the distal most portion of the elongate member 14 within the vasculature of a subject. It should be appreciated that the wall inserts 74, 76 can include any of the materials described herein with respect to the side inserts 58, 60 and/or the wall inserts 74, 76.

The septum extension insert 82 contacts blood exiting and entering the elongate member 14 through the axial openings 48, 50. The septum extension insert 82 may also be channeled for positioning over an end face of the septum extension 52 in a manner similar to that discussed in connection with the wall inserts 74, 76, and may have a curved atraumatic outer surface 84 which contacts blood during use.

As yet another example, while side inserts, wall inserts, and septum extension inserts have been described as including radiopaque material, other types of materials may additionally or alternatively be incorporated into the inserts. For example, one or more of the side inserts 58, 60, the wall inserts 74, 76, and the septum extension insert 82 may be impregnated or coated with anti-thrombogenic agents (e.g., heparin) to aid in the reduction of thrombus formation. As an additional or alternative example, one or more of the side inserts 58, 60, the wall inserts 74, 76, and the septum extension insert 82 may be coated with an antimicrobial, such as chlorhexadine or a solution containing silver.

Figure 12:
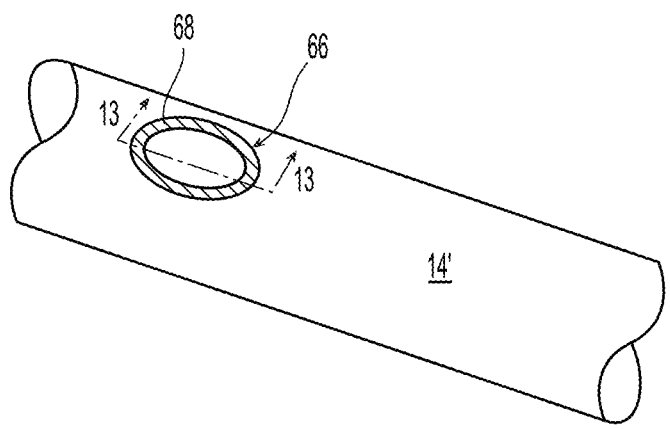
FIG. 12 is a perspective view of a portion of a catheter including a side insert.
Figure 13:
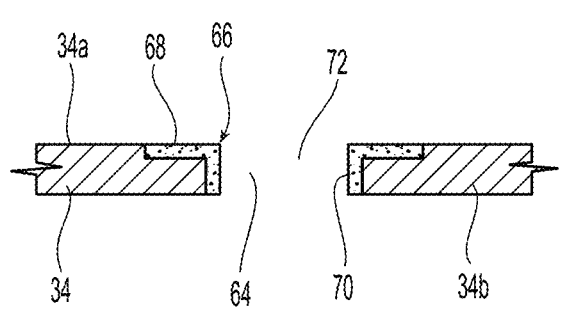
FIG. 13 is a cross-sectional view taken along the lines 13-13 of FIG. 12, with the side insert shown positioned within a side opening of an elongate member.
Figure 14:
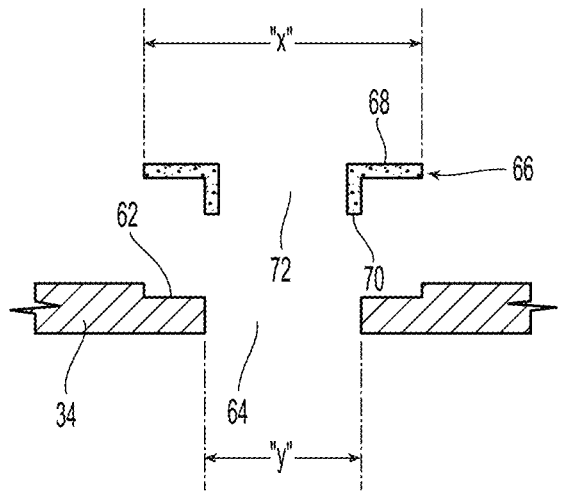
FIG. 14 is an exploded cross-sectional view of the side insert and elongate member of FIG. 12 along the lines 13-13 of FIG. 12.

As still another example, while side inserts have been described as having an outer boundary that generally approximates an internal boundary defined by a side opening of an elongate member, other configurations are additionally or alternatively possible. For example, referring now to FIGS. 12-14, an elongate member 14' may define a recess 62 at least partially surrounding a side opening 64 also defined by the elongate member 14'. The recess 62 and the side opening 64 may be, for example, oval-shaped. A side insert 66 includes an outer flange segment 68 and an inner flange segment 70. The outer flange segment 68 is dimensioned to be accommodated within the recess 62 of the elongate member 14' (e.g., through an interference fit), and defines an outer boundary "x" greater than the inner boundary "y" of the side opening 64. The inner segment 70 at least partially defines a flow passage 72 extending through the side insert 66. The outer perimeter of the inner segment 70 may approximate the side opening 64 defined by the elongate member 14'.

As compared to a side insert without a flange, the outer flange segment 68 and the inner segment 70 of the side insert 66 increases the surface area in contact with blood exiting and entering the elongate member 14'. Such increased surface area can, for example, enhance the anti-thrombogenic and/or antimicrobial effect of the side insert 66 (to the extent impregnated or coated with these agents).

The recess 62 in the wall of the elongate member 14' and the corresponding dimensioning of the outer flange segment 68 of the side insert 66 can result in a substantially continuous profile (e.g., varying by less than about 2%) from the side insert 66 and an outer surface of the elongate member 14'. This substantially continuous profile can reduce the potential of blood shear and/or the formation of thrombosis adjacent the side insert 66.

As yet another example, while catheter assemblies have been described as used in hemodialysis procedures, the use of catheter assemblies in one or more of a variety of medical procedures is additionally or alternatively possible. For example, catheter assemblies described herein can be used for administration or withdrawal of fluids such as medication, saline, bodily fluids, blood and urine in a range of catheter applications including surgical, diagnostic, and related treatments of diseases or body ailments of a subject. Examples of additional or alternative catheter applications include peritoneal dialysis, cardiac, abdominal, urinary, and intestinal applications.

A number of embodiments have been described. Nevertheless, it will be understood that various modifications may be made without departing from the spirit and scope of the disclosure. Accordingly, other embodiments are within the scope of the following claims.

What is claimed is:

1. A medical catheter comprising:
an elongate member including proximal and distal end portions and defining a longitudinal axis extending through the proximal and distal end portions, the elongate member including a wall at least partially defining a first lumen and a second lumen, and the wall defining a first side opening in fluid communication with the first lumen and a second side opening in fluid communication with the second lumen, wherein the first lumen extends from a first proximal opening of the elongate member to a first distal opening of the elongate member, the first side opening being between the first proximal opening and the first distal opening, and wherein the second lumen extends from a second proximal opening of the elongate member to a second distal opening of the elongate member, the second side opening being between the second proximal opening and the second distal opening;
a first insert at least partially disposed within the first side opening; and
a second insert at least partially disposed within the second side opening, the elongate member comprising a first material defining the first and second side openings, and the first and second inserts each comprising a second material different from the first material.

2. The medical catheter of claim 1, wherein the second material is more radiopaque than the first material.

3. The medical catheter of claim 2, wherein at least one of the first insert or the second insert is impregnated with an anti-thrombogenic agent.

4. The medical catheter of claim 1, wherein the second material has a higher durometer than the first material.

5. The medical catheter of claim 1, wherein the second material comprises at least one of titanium, stainless steel, polytetrafluoroethylene, or polyurethane having a Shore A hardness greater than 95 durometer.

6. The medical catheter of claim 1, wherein the second material comprises at least one of an anti-thrombogenic agent or an antimicrobial agent.

7. The medical catheter of claim 1, wherein the wall is an outer wall of the elongate member.

8. The medical catheter of claim 1, wherein the first and second side openings are disposed more toward the distal end portion than toward the proximal end portion of the elongate member.

9. The medical catheter of claim 1, wherein at least one of the first insert or the second insert has an outer boundary greater than an inner boundary of the respective first or second side opening.

10. The medical catheter of claim 1, wherein the first insert defines an insert passage in fluid communication with the first lumen and has at least one radiused surface along the insert passage.

11. The medical catheter of claim 10, wherein the at least one radiused surface defines a blood contacting surface, the radiused surface being configured to reduce shear stresses on blood entering or leaving the elongate member through the insert passage.

12. The medical catheter of claim 1, wherein at least one of the first insert or the second insert comprises a radiopaque core at least partially disposed within a polymer.

13. The medical catheter of claim 1, wherein the first insert and the second insert each defines a passage defining a flow passage for passage of blood, the respective one of the first insert or the second insert being configured to provide at least an anti-thrombotic effect on the blood entering or leaving the respective first or second lumen through the flow passage.

* * * * *